(12) United States Patent
Breitenbach et al.

(10) Patent No.: US 6,318,650 B1
(45) Date of Patent: Nov. 20, 2001

(54) METHOD FOR PRODUCING SMALL-PARTICLE PREPARATIONS OF BIOLOGICALLY ACTIVE SUBSTANCES

(75) Inventors: Jörg Breitenbach, Mannheim; Hans Dieter Zettler, Grünstadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,513

(22) PCT Filed: May 13, 1998

(86) PCT No.: PCT/EP98/02821

§ 371 Date: Nov. 15, 1999

§ 102(e) Date: Nov. 15, 1999

(87) PCT Pub. No.: WO98/52684

PCT Pub. Date: Nov. 26, 1998

(30) Foreign Application Priority Data

May 22, 1997 (DE) ............................................. 197 21 467

(51) Int. Cl.[7] ................................................... B02C 19/12
(52) U.S. Cl. ............................ 241/23; 241/65; 241/260.1
(58) Field of Search ................... 241/23, 65; 424/260.1, 424/485, 501

(56) References Cited

U.S. PATENT DOCUMENTS

| | | |
|---|---|---|
| 4,607,797 | 8/1986 | Enikolopow et al. . |
| 5,667,807 | 9/1997 | Hurner et al. . |

FOREIGN PATENT DOCUMENTS

| | | |
|---|---|---|
| 3332629 | 3/1985 | (DE) . |
| 19522899 | 12/1996 | (DE) . |
| 578 603 | 1/1994 | (EP) . |
| 582 300 | 2/1994 | (EP) . |
| 629 479 | 12/1994 | (EP) . |
| 686 392 | 12/1995 | (EP) . |
| WO-97/00673 * | 1/1997 | (EP) . |

* cited by examiner

Primary Examiner—Mark Rosenbaum
(74) Attorney, Agent, or Firm—Keil & Weinkauf

(57) ABSTRACT

A process for the continuous production of solid, particulate preparations of bioactive substances, in which the bioactive substances are homogeneously dispersed in a matrix of thermoplastic auxiliaries, in a screw extruder divided into a plurality of zones, wherein there is firstly melting of the matrix auxiliaries and mixing of the bioactive components with the matrix auxiliaries in a heatable zone, after which the mixture is cooled, precomminuted and finely ground in a cooling zone, the screw geometry in the cooling zone being selected so that the cooling zone consists of a conveying zone, a mixing zone and a kneading zone.

17 Claims, 1 Drawing Sheet

Figure 1:
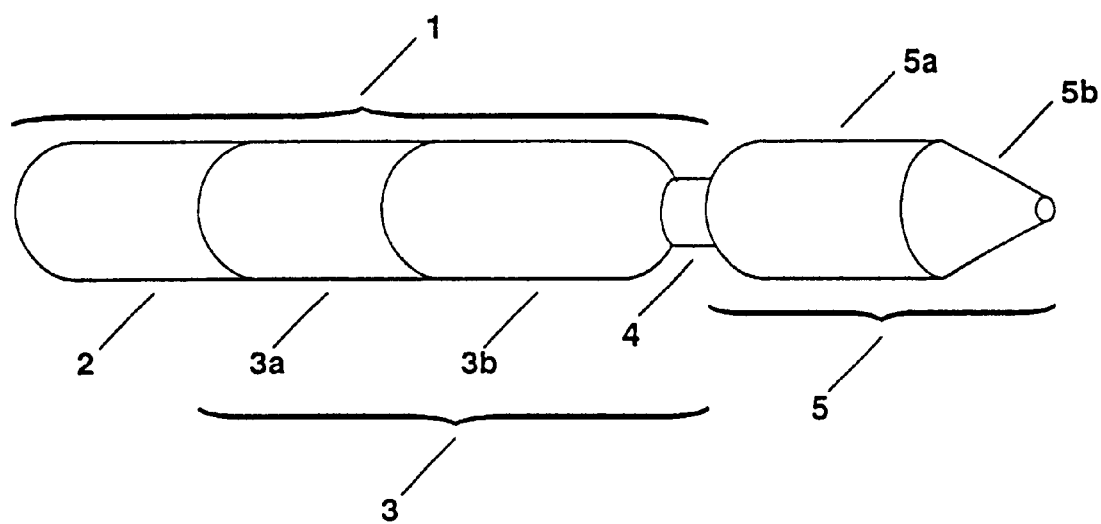

METHOD FOR PRODUCING SMALL-PARTICLE PREPARATIONS OF BIOLOGICALLY ACTIVE SUBSTANCES

The present invention relates to a process for the continuous production of small-particle preparations of bioactive substances, in which the bioactive substances are homogeneously dispersed in a matrix of thermoplastic auxiliaries, in an extruder divided into a plurality of zones. The invention furthermore relates to an arrangement for the continuous production of corresponding preparations.

The production of powders which contain active substances or other small-particle forms by conventional processes is often very costly and thus of no economic interest because of the number of steps in the processes and the problems of dust at the interfaces between the various steps in the processes.

DE-C 33 32 629 discloses a process for the production of a powder of polymers, where the polymers are melted in a twin-screw extruder, cooled, precrushed and finely ground. This process relates in particular to the powdering of polyethylene.

It is generally known to produce preparations containing active substances by the melt extrusion process.

EP-A 686 392 describes the production of pharmaceutical preparations by extrusion of mixtures containing active substances, with the extrudate subsequently being cold-cut and comminuted to granules.

DE-A 195 22 899 discloses a process for the continuous sintering of pharmaceutical granules, in which the mixture of components is initially partially sintered in the extruder and then conveyed toward the open face of the extruder. The resulting granules are then screened if necessary. However, this process requires the use in every case of lipoid components and does not describe the specific production of comminuted formulations.

The problem with processes of this type is that, on cooling the melts, on the one hand inhomogeneity may occur because the physical properties often differ widely, but on the other hand when oligomeric or polymeric substances are used there may also be a reduction in molecular weight. The homogeneity of the product is often unsatisfactory too.

It is an object of the present invention to find a process for the continuous production of particulate preparations of bioactive substances which results in stable homogeneous preparations, irrespective of the composition, in a straightforward manner.

We have found that this object is achieved by a process for the production of small-particle preparations of bioactive substances, in which the bioactive substance is homogeneously dispersed in a matrix of thermoplastic auxiliaries, in a screw extruder divided into a plurality of zones, wherein there is firstly partial sintering or melting of the matrix auxiliaries and mixing of the bioactive substances with the matrix auxiliaries in a heatable zone, after which the mixture is cooled, precomminuted and finely ground in a cooling zone, the screw geometry in the cooling zone being selected so that the cooling zone has a conveying zone as first zone, followed by a mixing zone and/or a kneading zone.

We have furthermore found an arrangement for carrying out the process according to the invention, which consists of a mixing and cooling unit and of a collecting unit, where the mixing and cooling unit and the collecting unit are connected together to form a system which is closed to the outside, and the mixing and cooling unit consists of an extruder which has heatable and coolable zones and whose discharge opening feeds into the collecting unit which consists of a cylindrical container provided with a conical discharge cylinder.

The process is carried out according to the invention in a screw extruder. The extruder may be a single-screw or multiple-screw extruder, preferably a twin-screw extruder, which is particularly preferably corotating and closely intermeshing.

The screw geometry in the heating zone of the extruder, in which the mixing and the melting or initial sintering take place, can be chosen to be closely intermeshing, intermeshing or non-intermeshing, with closely intermeshing screw geometry being preferred. The screws may rotate in opposite directions or, preferably, in the same direction. In the mixing and melting region, besides conveying elements there are preferably mixing and kneading elements arranged on the screws. Conveying elements are single- and multi-flight screw elements which differ in pitch. Mixing elements are gear-like toothed disk elements or backward-conveying elements provided with perforations, it being possible for some of the perforations to extend as far as the screw root or take up at least half of the helical radius.

Kneading elements are bicuspid or tricuspid disks, with the elements always having a plurality of disks which differ in width and have a differing angle of offset to one another.

The temperature in the mixing and melting zone may be, depending on the mixtures to be processed, in the range from 18 to 300, preferably 30 to 2000° C.

The cooling zone which follows the heating zone essentially consists initially of a conveying zone which is followed by a mixing zone and/or a kneading zone.

It is crucial for success of the process that pure conveying elements are employed in the first part of the cooling zone, in order to minimize the energy input and reduce the shear stress and to maximize the rate of cooling of the melt below the softening point. The conveying region of the cooling zone can be followed directly by a kneading zone to comminute the composition but preferably, in the direction of flow, initially by a mixing zone with mixing elements and then by a kneading zone to comminute the composition.

The jacket of the cooling zone is cooled with a liquid coolant. The temperature in the conveying zone of the cooling zone is preferably adjusted to 5 to 30° C. below the softening point of the composition to be cooled. It is possible for the temperature to be reduced over the entire cooling zone in the direction of flow by up to 150° C. below the softening point, depending on the softening point of the compositions. It may also be advisable for shock cooling to take place in the mixing region of the cooling zone and to cool the jacket to temperatures in the range from −10° C. to +10° C.

To avoid large temperature gradients over the flight cross-section, mixing elements are preferably employed, for example elements conveying in opposite directions and having wide perforations which effect rearrangement of the composition, particularly preferably after one third of the length of the cooling zone. After the temperature of the composition has fallen below the softening point, the solidified composition is comminuted and ground to particulate preparations in the last third of the cooling zone by using bicuspid or tricuspid disks, which may be interrupted by conveying elements.

It is also possible where appropriate to incorporate short conveying elements between the mixing zone and kneading zone, just as it may be advisable to provide short conveying sections between the mixing elements or the kneading elements.

The detailed screw geometry also depends on the sequence of addition of the components and, in specific cases, on the type of aids used.

In the case where a premix of matrix materials, additives and bioactive substances is introduced into the extruder, the screw geometry of the mixing and melting zone (heating zone) is preferably chosen so that initially conveying elements convey the mixture onward, then the mixture is melted in a region in which there are mainly kneading elements, with or without return conveying elements, after which, in the following cooling zone, there are initially a conveying zone, a mixing zone and a comminuting zone.

In another possible design of the process, initially matrix auxiliaries and other additives are metered into the extruder, conveyed in the direction of flow by means of conveying elements, and melted in a region in which mixing elements predominate. Then a mixture of bioactive substance and, where appropriate, a release agent is metered in and homogenized with the melt in another mixing region. The temperature in the homogenizing region can be higher or lower than in the first mixing region. It is preferably lower. The homogeneous melt mixture is then cooled and comminuted in the cooling zone. The addition of a release agent may produce defects in the cooling material, which facilitate the comminution process.

Another design of the process relates to mixtures into which a blowing agent is metered. A premix of matrix auxiliaries and bioactive substances is metered into the extruder, conveyed in the direction of flow and melted. Within the heating zone, the melting zone is followed by a conveying zone and then by a mixing zone in which the blowing agent is added. This is followed by the cooling zone. The mixing zone of the heating zone and the first part of the cooling zone (conveying zone) are shut off in the direction of flow by baffles. Baffles are return-conveying elements or kneading disks with return-conveying characteristics. Use of the baffles generates a pressure such that foaming does not take place until the second zone of the cooling zone (mixing zone). The foaming process effectively assists the comminution process.

The cooling zone is then followed by conveying elements in order to discharge the cooled and comminuted composition out of the extruder. The products can be discharged through an open extruder head. In a preferred embodiment, the conveying elements at the extruder outlet project beyond the screw channel, preferably by 0.5 to 1.5 times the screw diameter. It is also possible furthermore for a simple barrel flange to connect the last extruder flange to a continuing flange of a collecting device. In this connection, it is preferred for the particulate products from the two screw channels to be fed together in this adapting flange, so that a single bore is then sufficient for conducting the product stream. A compressed air device can also be attached to this adapting flange to convey the product away from the extruder head by a stream of air. The product can be separated from the stream of air later by using an air separator.

It is possible by the process according to the invention to produce preparations with particle sizes in the range from 0.001 to 50 mm diameter. Depending on the choice of the screw diameter, the mixing and kneading elements and the screw speeds, the resulting particles are coarse (10 to 50 mm), medium coarse (1 to 3 mm), small (0.3 to 1 mm), fine (0.1 to 0.3 mm), dense (0.03 to 0.1 mm) or microcrystalline (0.001 to 0.03 mm). The particle sizes are preferably from 0.001 to 10, particularly preferably 0.1 to 3, mm. The particle sizes adjusted in particular cases depend principally on the required range of applications. The particulate preparations display good uniformity in the particle size distribution so that they can be processed further without other screening processes. This can be established by screen analysis. A good uniformity of the particle size distribution is advantageous for the flow properties of the products and is important in particular for the direct tabletability of the powders or granules.

Crucial for product quality is also the uniformity of mass of the preparations, because the aim is to avoid not only overly high dust contents but also, in particular, inhomogeneity of the components. This is particularly important for the storage stability of the products. It is possible by specific choice of the screw geometry in the cooling zone to avoid inhomogeneity of the components just as much as a reduction in the molecular weight of oligomeric or polymeric constituents of the mixture.

The invention also relates to an arrangement for continuously producing preparations of bioactive substances, which consists of a mixing unit and of a collecting unit, where the mixing and collecting units are connected to form a system which is closed to the outside, and the mixing unit consists of a screw extruder as described above with heating and cooling zone for mixing and comminuting the components, where the discharge opening of the mixing unit feeds into the collecting unit, which consists of a cylindrical container provided with a conical discharge funnel. Mixing unit and collecting unit can be connected together by a welded seam or, preferably, by a flange.

This arrangement prevents in a simple manner contamination of the preparations by impurities in the air of the room. This is a great advantage particularly in the production of pharmaceutical preparations which must comply with GMP requirements (GMP: Good Medical Practice).

In a preferred embodiment of the arrangement, the conical discharge funnel of the collecting unit feeds directly into a conveying screw which transports the particulate material away. In another embodiment of the arrangement, a packaging or shaping unit directly follows the conveying screw.

It is possible to employ as shaping unit a conventional tableting press or an encapsulation arrangement. It is furthermore also possible for another screw extruder with calendering device to serve as shaping unit, in which the particulate preparation is mixed with other auxiliaries and/or bioactive substances and melted and, while still in the plastic state, shaped in the calendering device. This process is particularly advantageous if the bioactive substance is, before the incorporation into the final form, for example to be incorporated into a specific matrix, or for processing mutually incompatible substances.

The particulate preparations can, however, also be packaged directly in a packaging unit in barrels, canisters, big bags, bags or sacks.

It is possible with the aid of the arrangement according to the invention to obtain any desired preparation forms on-line in a simple manner.

It is, of course, also possible for the particulate preparations produced in the extruder not to be isolated first but, following the comminution step in the cooling zone, to be further processed directly in the extruder. This may be important especially when the bioactive substances must, before incorporation into the final dosage form, undergo small-particle preformulation in order to avoid incompatibilities with the matrix of the dosage form. Thus, the mixing and/or kneading zone can be followed by another extruder zone in which the powders or granules are mixed with other matrix auxiliaries, in particular with low-melting auxiliaries such as polyethylene glycols, fats or waxes, for example to produce plasters, suppository matrices or gels. The plastic compositions obtained in this way can then be extruded in a conventional way through a die or breaker plate and be shaped by hot or cold cutting, calendering or film blowing.

The process according to the invention and the arrangement according to the invention are suitable for producing particulate preparations of biological substances. Bioactive substances according to the invention are substances which have a biological effect in living organisms.

The process according to the invention is suitable, for example, for formulating the following substances or their physiologically acceptable salts, it also being possible to produce the salts in situ in the extruder:

antiinfectives aciclovir, aminoglycosides, amphotericin B, azole antimycotics, clotrimazole, itraconazole, sepraconazole, clindamycin, cephalosporins, chloramphenicol, erythromycin, 5-fluorouracil, etoposide, flucytosine, ganciclovir, griseofulvin, gyrase inhibitors, isoniazid, lincosamides, mebendazole, mefloquine, metronidazole, nitroimidazoles, novobiocin, platinum compounds, polymyxin B, praziquantel, pyrimethamine, rifamipicin, saquinavir, streptomycin, sulfonamides, tetracyclines, trimethoprim, vancomycin, zidovudine;

antipyretics, analgesics, antiinflammatory agents, paracetamol, ibuprofen, ketoprofen, oxaprozin, acetylsalicylic acid, morphine, propoxyphene, phenylbutazone;

antibiotics rifampicin, griseofulvin, chloramphenicol, cycloserine, erythromycin, penicillins such as penicillin G, streptomycin, tetracycline;

antiepileptics hydantoins, carbamazepine;

antitussives and antiasthmatics diphenhydramine;

antirheumatics chloroquine, indomethacin, gold compounds, phenylbutazone, oxyphenbutazone, penicillamine;

hypnotics barbiturates, phenobarbital, zolpidem, dioxopiperidines, ureides;

insecticides aldrin, dieldrin, chlorophenothane, hexachlorocyclohexane;

herbicides vinclozolin, strobilurins;

psychopharmaceuticals, neuroleptics perazine, promazine, sulpiride, thioridazine, chlorpromazine, meprobamate, triflupromazine, melperone, clozapine, risperidone, reserpine;

tranquilizers;

antidepressants imipramine, paroxetine, viloxazine, moclobemide;

psychostimulants;

psychomimetics;

diuretics potassium canrenoate, loop diuretics, furosemide, hydrochlorothiazide, spironolactone, thiazides, triamterene;

hormones androgens, antiandrogens, gestagens, glucocorticoids, estrogens, cortisol, dexamethasone, prednisolone, testosterone, Adiuretin, oxytocin, somatropin, insulin;

immunosuppressants ciclosporin;

bronchodilators;

muscle relaxants, tranquilizers carisoprodol, tetrazepam, diazepam, chlordiazepoxide;

enzymes lipase, phytase;

antigout agents allopurinol, colchicine;

anticoagulants coumarins;

antiepileptics phenytoin, phenobarbital, primidone, valproic acid, carbamazepine;

antihistamines chlorphenoxamine, dimenhydrinate;

antimimetics;

antihypertensives, antiarrhythmics lidocaine, procainamide, quinidine, calcium anatagonists, glycerol trinitrate, isosorbide dinitrate, isosorbide 5-mononitrate, pentaerythrityl tetranitrate, nifedipine, diltiazem, felodipine, verapamil, reserpine, minoxidil, captopril, enalapril, lisinopril;

sympathomimetics norfenefrine, oxedrine, midodrine, phenylephrine, isoprenaline, salbutamol, clenbuterol, ephedrine, tyramine, β-blockers such as alprenolol, metoprolol, bisoprolol;

antidiabetics biguanides, sulfonylureas, carbutamide, tolbutamide, glibenclamide, metformin, acarbose, troglitazone;

iron preparations;

vitamins vitamin C, B, A, D, folic acid;

ACE inhibitors captopril, ramipril, enalapril;

anabolic agents;

iodine compounds;

X-ray contrast agents;

CNS-active compounds;

antiparkinson agents biperiden, benzatropine, amantadine, opioid analgesics, barbiturates, benzodiazepines, disulfiram, lithium salts, theophylline, valproate, neuroleptics;

cytostatics;

antispasmolytics;

vasodilators naftidrofuryl, pentoxifylline.

It is also possible to obtain preparations of the bioactive substances in the form of solid solutions. The term solid solutions is familiar to the skilled worker (see Chiou and Riegelman, J. Pharm. Sci. 60 (1971) 1281–1302). The active substance in solid solutions of pharmaceutical agents in polymers or other matrices is in the form of a molecular dispersion in the matrix.

The active substance contents may vary within wide limits depending on the efficacy and rate of release. The only condition is that they suffice to achieve the desired effect. Thus, the active substance concentration can be in the range from 0.1 to 98, preferably from 0.5 to 70, % by weight. These data also apply in the same way for food supplements such as vitamin products.

The following substances can be employed as auxiliaries for the matrix:

In principle, all substances which can be softened by melting can be employed as receiving matrix. If the substances are polymers, they can, where appropriate, also be melt-processable at lower temperatures due to the addition of suitable aids.

The matrix into which particles can be embedded during the extrusion process may consist, for example, of polymers such as polyvinylpyrrolidone or copolymers of vinylpyrrolidone with vinyl acetate, acrylic acid or acrylic esters, eg. methyl acrylate/ethyl acrylate copolymers, polyethylene, polyisobutylene, polyethylene glycols, polyethylene oxide, polyethylene glycol/propylene glycol copolymers, polyvinyl alcohol, polyvinyl acetate, partially hydrolyzed polyvinyl acetate, cellulose ethers such as ethyl, methyl or hydroxypropyl cellulose ethers, hydroxypropylcellulose (Klucel brands supplied by Hercules), hydroxypropylmethylcellulose, hydroxypropylcellulose or cellulose esters, hydroxypropylmethylcellulose phthalate, gelatin, alginates and alginic acids, pectins, chitin, chitosan, vinyl acetate/ethylene copolymers, vinyl acetate/crotonic acid copolymers or mixtures of these polymers. The matrix polymers are preferably soluble in water but are at least swellable in water. Soluble in water means that at least 0.5 g, preferably at least 2 g, of the polymer dissolve, where appropriate to give colloidal or micellar solutions, in 100 g of water at 20° C.

Further conceivable polymer matrices are those which are absorbed or else degraded in the body. These include polylactic acid and its copolymers and, for example, poly(ortho) esters and polyamides, polyphosphazenes and polyurethanes.

However, the matrices obtained from sugar alcohols such as erythritol, sorbitol, mannitol, isomalt, or mono- and disaccharides such as fructose and glucose, or else fatty acid glycerides and/or fatty acid polyethylene glycol esters, as marketed, for example, under the names Gelucirs® (Gattefosse) or Precirols®, are also suitable. It is also possible in particular to use starches and their degradation products such as maltodextrins or natural celluloses.

Examples of pharmaceutical auxiliaries are bulking agents, lubricants, mold release agents, plasticizers, blowing agents, stabilizers, dyes, extenders, flow regulators and mixtures thereof. However, in principle, these pharmaceutical auxiliaries must not restrict the inventive concept of a successively dissolving or at least eroding, disintegrating drug form surrounded with a gel layer in the digestive fluids.

Examples of bulking agents are inorganic bulking agents such as the oxides of magnesium, aluminum, silicon, titanium etc. in a concentration of from 0.02 to 50, preferably from 0.20 to 20, % of the total weight of the drug form.

Examples of lubricants are stearates of aluminum, calcium and magnesium, and talc and silicones in a concentration of from 0.1 to 5, preferably from 0.1 to 3, % of the total weight of the form.

Examples of disintegration promoters which can be employed are sodium carboxymethyl starch or crospovidone. It is also possible to employ wetting agents such as sodium lauryl sulfate or sodium docusate.

Examples of plasticizers include low molecular weight poly(alkylene oxides) such as poly(ethylene glycols), poly (propylene glycols), poly(ethylene/propylene glycols); organic plasticizers with a low molecular weight such as glycerol, pentaerythritol, glycerol monoacetate, diacetate or triacetate, propylene glycol, sodium diethyl sulfosuccinate etc., added in concentrations of from 0.5 to 15, preferably from 0.5 to 5, % of the total weight of the drug form.

Examples of dyes are known azo dyes, organic and inorganic pigments or coloring agents of natural origin.

Inorganic pigments are preferably present in concentrations of from 0.001 to 10, preferably from 0.5 to 3, % of the total weight of the drug form.

It is furthermore possible to add other additives which improve the flow properties of the mixture or act as mold release agents, such as: animal or vegetable fats, preferably in their hydrogenated form, especially those which are solid at room temperature. These fats preferably have a melting point of 50° C. or above. Triglycerides of $C_{12}$, $C_{14}$, $C_{16}$ and $C_{18}$ fatty acids are preferred. The same function can also be carried out by waxes such as carnauba wax. These additives can be added alone without the addition of bulking agents or plasticizers. These fats and waxes can advantageously be admixed alone or together with mono-and/or diglycerides or phosphatides, especially lecithin. The mono- and diglycerides are preferably derived from the types of fats described above, ie. $C_{12}$, $C_{14}$, $C_{16}$ and $C_{18}$ fatty acids. The total amount of fats, waxes, mono- and diglycerides and/or lecithins is from 0.1 to 30, preferably 0.1 to 50, % of the total weight of the drug form.

Flow regulators which can be used are, for example, Aerosils or talc.

It is furthermore possible to add stabilizers such as antioxidants, light stabilizers, hydroperoxide destroyers, radical scavengers and stabilizers against microbial attack.

Auxiliaries for the purpose of the invention also mean substances to produce a solid solution containing the pharmaceutical agent. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate and citric and succinic acids, bile acids, sterols and others as indicated, for example, in J. L. Ford, Pharm. Acta Helv. 61 (1986) 69–88.

Additions of bases or acids to control the solubility of an agent are also regarded as pharmaceutical auxiliaries (see, for example, K. Thoma et al., Pharm. Ind. 51 (1989) 98–101).

When polymeric binders are used, they should soften or melt or be sinterable in the complete mixture of all the components in the range from 10 to 250, preferably from 30 to 180, ° C., so that the composition can be extruded. The melts are preferably solvent-free.

It is also advantageous in general to admix one or more substances which are able to act as blowing agents, for example to add citric acid or basic substances such as carbonates, specifically alkali metal carbonates. A blowing agent effect can also be achieved by adding basic compounds to acidic agents or acids to basic agents. It is also possible furthermore to add gaseous blowing agents to the molten compositions.

The process is suitable according to the invention for producing particulate pharmaceutical mixtures, cosmetic formulations, crop protection compositions, fertilizers, veterinary medical mixtures, foods for livestock, for example fish feeds, or food supplements and dietetic foods.

The pharmaceutical mixtures may be, for example, dusting powders or ointment ingredients, furthermore instant granules, sachets or bases for drinkable suspensions or syrups. Preparations in powder or granule form are of great practical importance in particular for producing pediatric medicines.

The particulate preparations can also be incorporated into all conventional drug forms, for example into uncoated or coated tablets, suppositories, transdermal drug forms, and drug forms for inhalation, such as asthma remedies in powder form.

The process according to the invention is particularly suitable for incorporating flavorings, for example matrix-encapsulated terpenes.

EXAMPLES

Example 1

A mixture of 40% by weight of ibuprofen and 60% by weight of polyvinylpyrrolidone (K30) was extruded in a twin-screw extruder (ZSK 30, Werner Pfleiderer) with an output of 10 kg/h. The individual sections in the heating zone were at 40, 70, 90, 100 and 100° C. The first section in the cooling zone was at 70° C. The cooling zone consisted of two sections in the region of which the extruder screws contained pure conveying elements, with the second section being at 60° C., and of a comminuting zone of three sections. In this region, the screws were composed of tricuspid disks. The temperature of the individual sections in the direction of conveyance was 50° C., 30° C. and 20° C. The resulting granules had an average particle size of 0.7 mm. The granules contain the agent in the form of a molecular dispersion.

Example 2

A mixture of 60% by weight of ibuprofen and 40% by weight of maltodextrin CPUR 01612 (Cerestar) was extruded in a twin-screw extruder (ZSK 30, Werner Pfleiderer) with an output of 5 kg/h. The individual sections in the heatng zone were at 60, 80, 90, 120 and 120° C. The first section in the cooling zone was at 60° C. The configuration and the design, and the temperature of the subsequent sections, were chosen as in Example 1. The resulting granules had an average particle size of 0.4 mm.

zone were at 60, 80, 90, 110 and 120° C. The first section in the cooling zone was at 90° C.

The cooling zone consisted of two sections in the region of which the extruder screws contained pure conveying elements. The second section was at 70° C. The comminuting zone consisted of three sections. In this region, the screws were composed of bicuspid disks. The temperature of the individual sections in the direction of conveyance was 60° C., 40° C. and 25° C. The resulting granules had an average particle size of 0.8 mm.

Example 4–8

| Agent 1 | Agent 2 | Polymer 1 | Polymer 2 | Auxiliary (2) | Temp. [° C.] Zone 1 | Temp. [° C.] Zone 2 |
| --- | --- | --- | --- | --- | --- | --- |
| Paracetamol 60% by weight | Caffeine 10% by weight | Vinylpyrrolidone/vinyl acetate copolymer Kollidon ® VA64 5% by weight | Polyethylene oxide (Lutrol E 1500 from BASF AG) 5% by weight | Isomalt 19% by weight 1% strawberry flavor | 40, 70, 90, 100, 100 | 80, 70, 50, 30, 20 |
| Gallopamil hydrochloride 40% by weight | | Ethylcellulose Type NF 7 from Dow, USA, 50% by weight | | 10% by weight microcrystalline cellulose (Avicel ® from FMC, UCS) | 60, 80, 90, 100, 130 | 100, 90, 80, 50, 30 |
| Tramadol hydrochloride, 60% by weight | | Polyvinylpyrrolidone, K value 17 (Kollidon K 17 from BASF AG) 3% by weight | 35% by weight isomalt | 1% by weight crosslinked polyvinylpyrrolidone (Crospovidone from BASF AG), 0.5% by weight lecithin, 0.5% by weight sodium lauryl sulfate | 66, 75, 85, 98, 111 | 85, 70, 50, 40, 28 |
| Clotrimazole 60% by weight | | Vinylpyrrolidone/vinyl acetate copolymer Kollidon VA 64 | | 0.3% by weight sodium lauryl sulfate, 0.2% by weight Aerosil ® 200 C from Degussa AG) | 50, 70, 90, 100, 100 | 80, 60, 40, 30, 25 |
| Acyclovir mononitrate 40% by weight | | Polyacrylate (Eudragit ® 30 D, from Röhm) 3% by weight | Hydroxymethylcellulose 55% by weight | 2% by weight bentonite A, metered into the mixing zone | 80, 90, 90, 140, 150 | 100, 60, 40, 30, 30 |

Example 3

The components were fed separately through differential scales into the extruder. In this case, 50% by weight of theophylline and 40% by weight of hydroxypropylmethylcellulose (Klucel® supplied by Hercules, USA) and 10% by weight of polyethylene oxide (average molecular weight 6000, Lutrol® E 6000 supplied by BASF AG) were extruded in a twin-screw extruder (ZSK 30, Werner Pfleiderer) with an output of 8 kg/h. The individual sections in the heating

Example 9

Kollidon VA 64 was extruded in a twin-screw extruder (ZSK 30, Werner Pfleiderer) with an output of 5 kg/h. The configuration of the sections was chosen in this case so that initially only conveying took place. This was followed by melting. The individual sections in the heating zone were at 60, 80, 90, 120 and 130° C. In a downstream mixing zone whose screw elements consisted exclusively of conveying elements, the agent ketoprofen was metered in via differential scales at 2 kg/h through a flange with pressure equalization. The temperature in this region was kept at 130° C. The first section in the cooling zone was at 60° C. The subsequent configuration and design and the temperature were chosen as in Example 1. The resulting granules had an average particle size of 0.1 mm. DSC measurements revealed that the agent is embedded as a molecular dispersion in the cooled powder material because the agent melting peak no longer appeared.

We claim:

1. A process for the continuous production of solid, particulate preparations of bioactive substances, in which the bioactive substances are homogeneously dispersed in a matrix of thermoplastic auxiliaries, in a screw extruder having an extruder jacket, which extruder is divided into a plurality of zones, wherein the process comprises firstly melting the matrix auxiliaries and mixing the bioactive components with the matrix auxiliaries in a heatable zone of the extruder to form a mixture, and subsequently cooling, precomminuting and finely grinding the mixture in a cooling zone of the extruder to form a powder, wherein the screw geometry in the cooling zone is selected so that the cooling zone has a conveying zone as first zone, followed by a mixing zone and/or a kneading zone.

2. A process as claimed in claim 1, wherein the extruder jacket of the conveying zone of the cooling zone is cooled to a temperature which is 5 to 30° C. below the softening temperature of the mixture.

3. A process as claimed in claim 1, wherein the cooling zone has a conveying zone as first zone, followed in the direction of flow by first a mixing zone and then a kneading zone.

4. A process as claimed in claim 1, wherein the extruder jacket of the mixing zone and/or the kneading zone in the cooling zone is cooled to temperatures in the range from −10 to +10° C.

5. A process as claimed in claim 1, wherein a blowing agent is added in the heating zone after the components of the mixture have melted.

6. A process as claimed in claim 1, wherein a release agent is added to the mixture.

7. A process as claimed in claim 1, wherein the cooling zone is followed by a conveying zone having conveying elements to discharge the powder from the extruder, where the conveying elements project out of the screw channel by 0.5 to 1.5 times the screw diameter.

8. A process as claimed in claims 1, wherein the extruder is a corotating twin-screw extruder.

9. A process as claimed in claim 1, wherein the powder is discharged from the extruder through an extruder outlet into a cylindrical collecting container which container is provided with a conical discharge funnel, where the extruder outlet and the collecting container form a system which is closed to the outside.

10. A process as claimed in claim 9, wherein the conical discharge funnel feeds into a conveying screw which delivers the powder continuously to a shaping or packaging arrangement.

11. An arrangement for carrying out a process for the continuous production of solid, particulate preparations of bioactive substances, in which the bioactive substances are homogeneously dispersed in a matrix of thermoplastic auxiliaries, which arrangement consists of a mixing unit and a collecting unit, where the mixing unit and the collecting unit are connected together to form a system which is closed to the outside, and wherein the mixing unit consists of an extruder which has heatable and coolable zones and which has a discharge opening for feeding the extruder discharge into the collecting unit by means of conveying elements, and which collecting unit consists of a cylindrical container provided with a conical discharge funnel.

12. An arrangement as claimed in claim 11, wherein the conical discharge funnel feeds into a conveying screw.

13. An arrangement as claimed in claim 12, wherein the conveying screw is followed by a shaping or packaging unit.

14. An arrangement for carrying out a process for the continuous production of solid, particulate preparations of bioactive substances, in which the bioactive substances are homogeneously dispersed in a matrix of thermoplastic auxiliaries, which arrangement consists of a mixing unit and a collecting unit, where the mixing unit and the collecting unit are connected together to form a system which is closed to the outside, and wherein the mixing unit consists of an extruder which has heatable and coolable zones and which has a discharge opening for feeding the extruder discharge into the collecting unit by means of conveying elements, and which collecting unit consists of a cylindrical container provided with a conical discharge funnel, and in which the conveying elements at the extruder outlet project beyond the screw channel into the interior of the collecting zone.

15. An arrangement as claimed in claim 14, wherein the conveying elements project into the interior of the collecting zone by 0.5 to 1.5 times the screw diameter.

16. An arrangement as claimed in claim 14, wherein the conical discharge funnel feeds into a conveying screw.

17. An arrangement as claimed in claim 16, wherein the conveying screw is followed by a shaping or packaging unit.

* * * * *